United States Patent [19]

Bicoll

[11] Patent Number: 4,681,101
[45] Date of Patent: Jul. 21, 1987

[54] ANESTHETIC DEVICE

[76] Inventor: Norton J. Bicoll, 728 Preston Forest, Dallas, Tex. 75230

[21] Appl. No.: 767,521

[22] Filed: Aug. 20, 1985

[51] Int. Cl.4 .................. A61B 17/00; A61B 17/34
[52] U.S. Cl. ........................... 128/303 R; 128/329 A
[58] Field of Search .............. 128/303 R, 329 A, 325, 128/355, 329 R; D24/8, 10, 11, 23, 26, 28; 433/102, 72

[56] References Cited

U.S. PATENT DOCUMENTS

| D. 212,868 | 12/1968 | Olson et al. | D24/23 |
| D. 279,405 | 6/1985 | Lentz | D24/23 |
| 906,085 | 12/1908 | Tolman | 128/355 |
| 1,063,109 | 5/1913 | Bolls | 433/102 |
| 3,774,614 | 11/1973 | Cook | 128/325 |
| 3,905,375 | 9/1975 | Toyama | 128/329 A |
| 4,479,496 | 10/1984 | Hsu | 128/329 A |
| 4,520,798 | 6/1985 | Lewis | 128/329 A |
| 4,542,742 | 9/1985 | Winkelman et al. | 128/325 |

Primary Examiner—Richard J. Apley
Assistant Examiner—H. Macey
Attorney, Agent, or Firm—Kanz, Scherback & Timmons

[57] ABSTRACT

Disclosed is a device for temporarily anesthetizing localized regions of living tissue. The device includes a substantially disc-shaped flat body with an aperture therein and a shank for supporting the flat body. The flat body is placed on the surface of the living tissue to be anesthetized and pressure applied thereto with the shank. A puncture device may be inserted into the tissue through the aperture while the tissue is temporarily anesthetized.

2 Claims, 1 Drawing Figure

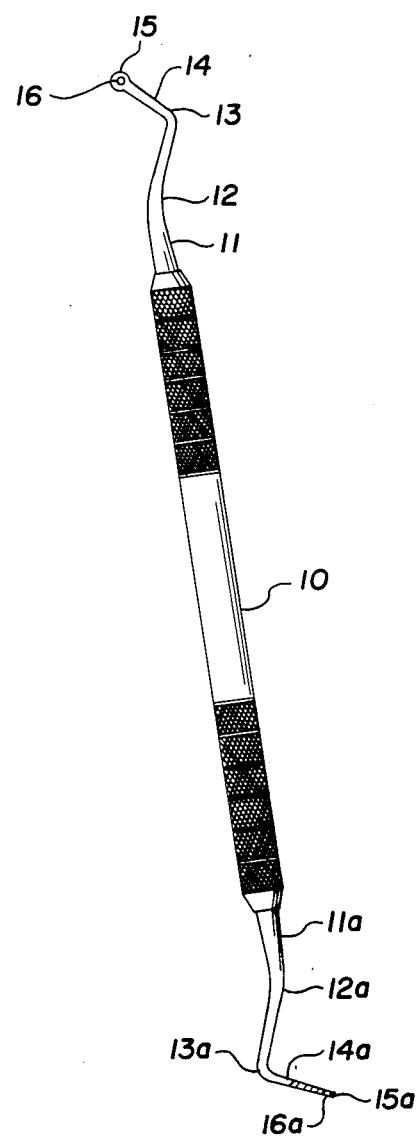

ANESTHETIC DEVICE

This invention relates to devices for temporarily anesthetizing living tissue. More particularly, it relates to methods of temporarily anesthetizing localized regions of living tissue to avoid the sensation of pain associated with inserting a puncture device such as an injection needle or cannula thereinto and to devices for practicing such methods.

The following disclosure is offered for public dissemination in return for grant of a patent. Although it is sufficiently detailed to provide full understanding of the principles of the invention, this disclosure is not intended to prejudice the purpose of a patent which is to protect each new inventive concept therein no matter how others may later disguise it by variations in form, additions or further improvements.

It is frequently necessary to insert a puncture device, such as an injection needle or cannula, into living tissue. For example, injection needles are commonly used to inject pharmacological solutions into living tissue for treatment of infection and to inject other solutions for immunization purposes. Similarly, cannulas are frequently inserted into living tissue to withdraw fluids from the tissue, such as for taking blood samples, etc. Injection needles are also commonly used to inject anesthetics into living tissue to temporarily anesthetize the tissue for surgical or otherwise painful operations on living tissue. Even though anesthetics may be applied with injection needles, initial insertion of the injection needle itself into the surface of the tissue for injection of the anesthetic can be quite painful.

Certain portions of the human body are more sensitive to pain than others because of the concentration of nerve endings in such regions. For example, the fingertips are quite sensitive. Likewise, most portions of the mouth, gums, etc. are also quite sensitive to pain. Unfortunately, whenever dental repairs, gum surgery or other surgery is required, local anesthetic must be applied to the affected regions. However, insertion of the anesthetic-injecting needle itself can be quite painful because of the high sensitivity of the oral regions.

In accordance with the present invention living tissue is temporarily effectively anesthetized without pain for a sufficent time period to permit the insertion of a puncture device thereinto. Once the injection needle has penetrated the initial barrier tissue, anesthetic fluids may be injected into the living tissue by the injection needle so that no pain is ever encountered during the needle injection process.

The process of the invention essentially relies on the phenomenon of pressure anesthesia whereby a localized portion of living tissue can be temporarily anesthetized by applying a moderate amount of pressure thereto. Utilizing this phenomenon, the invention provides a device adapted to exert moderate pressure on a localized area of living tissue. The instrument, however, has an aperture therein through which a puncture device, such as a needle or the like, may be inserted to puncture the locally anesthetized tissue. Accordingly, there is no sensation of pain whatsoever associated with the initial puncture. The apparatus of the invention may be readily formed from suitable conventional material such as surgical steel of the like and conveniently used in any situation wherein puncture of living tissue is required. Other features and advantages of the invention will become more readily understood from the following detailed description taken in connection with the appended claims and attached drawings which illustrate the preferred embodiment of an anesthetic tool for practicing the invention.

As illustrated in the sole FIGURE, a device for practicing the invention may be conveniently embodied in a double-ended (as illustrated) or single-ended elongated tool having a handle 10 appropriately designed to be easily manipulated by the user. A shank 11 extending from the handle 10 terminates in a substantially flattened head portion 15. In the preferred embodiment head 15 is substantially circular or disc-like and has an aperture 16 substantially centrally located therein.

The effectiveness of pressure anesthesia is related to the surface area of the tissue to which the pressure is applied as well as the amount of pressure applied thereto. Accordingly, it is preferred that the area of head 15 be maintained relatively small but sufficiently large so that is is not likely to cause skin rupture or other physical pain when moderate pressure is applied to the underlying tissue with the instrument. For this reason it is also preferred that all edges of the head 15 be smooth and rounded. Aperture 16 is preferably centrally located within the disc face of head 15 and has a diameter preferably of no more than about two to three times the diameter of the injection device to be used.

For use, the head 15 is applied directly to the human tissue and a moderate amount of pressure exerted thereon. The injection needle is then inserted directly through aperture 16 into the living tissue upon which pressure is being applied by the head 15. Since the localized area subjected to pressure by head 15 is temporarily locally anesthetized, the puncture entry of the injection device is not sensually observed by the living tissue. Once the injection needle is inserted into the living tissue, anesthetic can be injected into the adjacent tissue as the depth of the needle progresses, thereby avoiding any sensation of pain whatsoever.

In the preferred embodiment, the shaft 11 is substantially cylindrical but tapered in diameter from the handle 10 to the head 15. It is preferred that the head 15 be aligned substantially near the axis of the tool to aid in manipulation and use of the anesthetic device. To achieve this alignment, the shank 11 may be curved or bent in opposite directions at removed locations such as 12 and 13. In the preferred embodiment, the portion 14 of shank 11 between head 15 and curve 13 may also be somewhat flattened to provide a visual aid to the user in orienting the device.

As illustrated in the drawing, the preferred embodiment of the anesthetic tool of the invention includes a second shank 11a extending from the opposite end of handle 10. Shank 11a is identical to shank 11 including bends 12a and 13a. However, shank portion 14a and head 15a are rotated approximately ninety degrees with respect to the axis of shank 11a so that the axis of aperture 16a is substantially aligned parallel with the axis of the handle 10. It will be observed that the axis of aperture 16 is substantially ninety degrees from the axis of the handle 10. The rearrangement of head 15a with respect to head 15 is provided so that a single tool may be used to apply localized anesthetic pressure to various relatively inaccessible regions while permitting the user to visually observe the alignment of the needle and the aperture.

In the preferred embodiment the head 15 is circular to avoid corners which could accidentally inflict pain. Likewise, and for the same reasons, the head 15 is continuous and monolithic. It will be observed, however, that a U-shaped head would produce similar anesthetic results.

The diameter of the aperture 16 should be sufficient to permit the convenient insertion of an anesthetic needle or the like therethrough. In the preferred embodiment the diameter of the aperture is approximately one millimeter.

The diameter of the head 15 should be no greater than that required to continuously apply moderate pressure to the surface area of the tissue immediately surrounding the point of puncture without being so small as to be likely to cause discomfort itself when pressure is applied thereto. In the preferred embodiment the diameter of the head is about two to about four times the diameter of the aperture.

It will be observed that the device described may be conveniently used to temporarily locally anesthetize living tissue. While the invention has been described with particular reference to a specific embodiment, it will be realized that the device may be formed in various alternate configurations. Accordingly, it is to be understood that although the invention has been described with particular reference to specific embodiments thereof, the forms of the invention shown and described in detail are to be taken as preferred embodiments of same, and that various changes and modifications may be resorted to without departing from the spirit and scope of the invention as defined by the appended claims.

What is claimed:

1. A device for temporarily anesthetizing localized regions of living tissue comprising:
   (a) a first substantially flat smooth body having a first substantially circular aperture passing transversely therethrough, the largest diameter of said first aperture being approximately one millimeter and the diameter of said first body being approximately two to approximately four times the diameter of said first aperture;
   (b) a first elongated shank supporting said first substantially flat smooth body;
   (c) a second substantially flat smooth body having a second substantially circular aperture passing transversely therethrough, the largest diameter of said second aperture being approximately one millimeter and the diameter of said second body being approximately two to approximately four times the diameter of said second aperture;
   (d) a second elongated shank supporting said second substantially flat smooth body; and
   (e) an elongated handle interconnecting said first shank and said second shank with the central axis of said first aperture aligned substantially 90° from the axis of said elongated handle and the central axis of said second aperture aligned substantially parallel with the axis of said handle.

2. The method of temporarily anesthetizing a localized region of living tissue for insertion of a puncture device thereinto comprising the steps of:
   (a) locating a substantially flat smooth body of limited dimensions having a substantially circular central aperture passing transversely therethrough with the largest diameter of said aperture being approximately one millimeter on the surface of the localized region of living tissue to be anesthetized with location means extending laterally from said body so that only a small area of tissue is exposed through said aperture; and
   (b) applying pressure to said living tissue with said body immediately before and during the insertion of a puncture device into said living tissue through said aperture so that substantial pressure is applied to said living tissue immediately adjacent the point of entry of said puncture device.

* * * * *

UNITED STATES PATENT AND TRADEMARK OFFICE
CERTIFICATE OF CORRECTION

PATENT NO. : 4,681,101

DATED : July 21, 1987

INVENTOR(S) : Norton J. Bicoll

It is certified that error appears in the above-identified patent and that said Letters Patent is hereby corrected as shown below:

In Column 1, line 65    change "of" to ---or---

Signed and Sealed this

First Day of December, 1987

Attest:

DONALD J. QUIGG

*Attesting Officer*          *Commissioner of Patents and Trademarks*